United States Patent [19]

Smith, Jr.

[11] Patent Number: 4,849,569
[45] Date of Patent: Jul. 18, 1989

[54] ALKYLATION OF ORGANIC AROMATIC COMPOUNDS

[75] Inventor: Lawrence A. Smith, Jr., Houston, Tex.

[73] Assignee: Chemical Research & Licensing Company, Houston, Tex.

[21] Appl. No.: 258,892

[22] Filed: Oct. 17, 1988

Related U.S. Application Data

[60] Division of Ser. No. 122,485, Nov. 16, 1987, which is a continuation of Ser. No. 846,357, Mar. 31, 1986, abandoned, which is a continuation of Ser. No. 689,444, Jan. 7, 1985, abandoned.

[51] Int. Cl.$^4$ .................................................. C07C 2/64
[52] U.S. Cl. ...................................... 585/446; 585/458; 585/467; 568/790; 568/791; 568/793
[58] Field of Search .................. 585/446, 458, 467; 568/790, 791, 793

[56] References Cited

U.S. PATENT DOCUMENTS

| | | | |
|---|---|---|---|
| 4,215,011 | 7/1980 | Smith | 252/426 |
| 4,232,177 | 11/1980 | Smith | 585/324 |
| 4,242,530 | 12/1980 | Smith | 585/510 |
| 4,302,356 | 11/1981 | Smith | 252/426 |
| 4,307,254 | 12/1981 | Smith | 568/647 |
| 4,316,997 | 2/1982 | Vaughan | 585/458 |
| 4,371,714 | 2/1983 | Young | 568/791 |
| 4,423,254 | 12/1983 | Olah | 568/793 |
| 4,443,559 | 4/1984 | Smith | 502/527 |
| 4,469,908 | 9/1984 | Burress | 585/467 |
| 5,250,052 | 2/1981 | Smith | 252/426 |

Primary Examiner—Curtis R. Davis
Attorney, Agent, or Firm—Kenneth H. Johnson

[57] ABSTRACT

Aromatic compounds are alkylated in a catalytic distillation, wherein the catalyst structure also serves as a distillation component by contacting the aromatic compound with a $C_2$ to $C_{10}$ olefin in the catalyst bed under 0.25 to 50 atmospheres of pressure and at temperatures in the range of 80° C. to 500° C., using as the catalyst a mole sieve characterized as acidic or an acidic cation exchange resin. For example, ethyl benzene is produced by feeding ethylene below the catalyst bed while benzene is conveniently added through the reflux in molar excess to that required to react with ethylene, thereby reacting substantially all of the ethylene and recovering benzene as the principal overhead and ethyl benzene in the bottoms.

23 Claims, 1 Drawing Sheet

ALKYLATION OF ORGANIC AROMATIC COMPOUNDS

This invention was made with Government support under DE-FC07-80CS40454 awarded by the Department of Energy. The Government has certain rights in this invention.

This application is a division of Ser. No. 122,485 filed Nov. 16, 1987, which was a continuation of Ser. No. 846,357 filed Mar. 31, 1986 and now abandoned, which was a continuation of Ser. No. 689,444 filed Jan. 7, 1985 and now abandoned.

BACKGROUND OF THE INVENTION

1. Field of The Invention

The present invention relates to a process for the alkylation of organic aromatic compounds. More particularly the invention relates to a process for the concurrent alkylation and distillation of reaction components (reactants and products) in a catalyst bed wherein the catalyst also serves as the distillation structure.

2. Related Art

Recently a new method of carrying out catalytic reactions has been developed, wherein the components of the reaction system are concurrently separable by distillation, using the catalyst structures as the distillation structures. Such systems are described variously in U.S. Pat. Nos. 4,215,011 ; 4,232,530; 4:242,530; 4,250,052; 4,302/356; and 4;307;254 commonly assigned herewith.

Briefly, a structure described there is a cloth belt with a plurality of pockets spaced along the belt, which is then wound in a helix about a spacing material such as stainless steel knitted mesh. These units are then disposed in the distillation column reactor.

In addition, commonly assigned U.S. Pat. application, Ser. No. 307,120 filed Sept. 30, 1981, discloses a variety of catalyst structures for this use and is incorporated herein.

Ethylbenzene and cumene are currently produced by the reaction of benzene and the respective olefin, i.e., ethylene and propylene by acid catalysis. In some known processes the catalyst is highly corrosive and has a relatively short life, e.g., $AlCl_3$, $H_3PO_4$ on clay, $BF_3$ on alumina, and others require periodic regeneration, e.g., molecular sieves. The exothermicity of the reaction and the tendency to produce polysubstituted benzene require low benzene conversions per pass with large 20 volume recycle in conventional processes. Advantages of the present invention are that the catalyst 4 are not highly corrosive and do not require periodic regeneration, the heat of reaction is used efficiently, only low volume is required and the feed ratios can approach unity.

SUMMARY OF THE INVENTION

Briefly, the present invention is a process for the alkylation of organic aromatic compounds by contacting the organic aromatic compound and a $C_2$ to $C_{20}$ olefin in a distillation column reactor containing a fixed bed acidic Catalytic distillation structure in a distillation reaction zone thereby catalytically reacting said organic aromatic compound and said olefin to produce an alkylated organic aromatic product and concurrently in said fixed bed fractionating the resultant alkylated organic product from the unreacted materials. The catalytic distillation structure provides both the catalytic sites and the distillation sites. The alkylated organic aromatic product is withdrawn (rom the distillation column reactor at a point below the fixed bed and unreacted organic aromatic compound may be taken off as an overhead. Suitable acidic catalysts include molecular sieves (mole sieves) and cation exchange resins.

More specifically the mole sieve or cation exchange resin catalyst packing is of such a nature as to allow vapor flow through the bed, yet provide a sufficient surface area for catalytic contact as described in the previously noted U.S. Pat. application Ser. No. 307,120 filed Sept. 30, 1981, and U.S. Pat. Nos. 4,215,011 and, 4,302,356 which are incorporated herein in their entirety. The catalyst packing is preferably arranged in the upper portion of the distillation column reactor, more preferably occupying about one-third to one half of the column and extending substantially to the upper end thereof.

The exact location of the olefin feed will depend on the particular feeds and the desired product. In one embodiment the olefin feed to the reaction is preferably made below the catalyst bed thereby allowing mixing of the reactants before contact with the catalyst bed. In another embodiment the olefin feed to the reaction is preferably made into the catalyst bed thereby allowing immediate contact of this reactant with the organic aromatic compound in the catalyst to thereby react as much of the two as possible and reduce or eliminate the olefin leaving the reactor as overhead or bottoms, such as between the bottom of the fixed bed, and the upper one-fourhh section thereof preferably in the middle one-half of the bed. For example, in the case of alkylation of benzene (B.P. 80° C.) with propylene, the olefin feed may be located below the bed, whereas, for alkylation of benzene with decene (B.P.170° C.) the decene is preferably fed into the upper half of the bed.

The organic aromatic compound feed may be added at any point in the reactor, however, preferably it is added to the fixed bed or to the reflux as makeup. Also, in order to achieve high selectivity toward monosubstitution (which is a preferred aspect of the present invention), there is a large excess of the organic aromatic compound to the olefin in the reactor in the range of 2 to 100 moles of organic aromatic compounds per mole of olefin, that is the net molar feed ratio of aromatic organic compound olefin may be close to 1:1, although the system is operated so as to maintain a substantial molar excess of organic aromatic compound to olefin in the reaction zone. The alkylated product is the highest boiling material and is separated in the lower portion of the column usually as bottoms. The organic aromatic compound can be the second highest boiling or third highest boiling component (excluding inerts) as noted above, however, by operating with a large excess of the organic aromatic compound, the major portion of the olefin is reacted: thereby reducing the separation and recovery problems. The success of catalytic distillation lies in an understanding success of catalytic distillation lies in an understanding of the principles associated with distillation. First, because the reaction is occurring concurrently with distillation, the initial reaction product is removed from the reaction zone as quickly as it is formed. The removal the alkylation product minimizes polysubstitution, decomposition of the alkylation product and/or oligomerization of the olefin. Second, because the organic aromatic compound is boiling, the temperature of the reaction is controlled by the boiling point of that component at the system pressure. The heat of the reaction simply creates more boil up, but no increase in temperature. Third, the reaction has an increased driving force because the reaction products have been removed and cannot contribute to a reverse reaction (Le Chatelier's Principle).

As a result, a great deal of control over the rate of reaction and distribution of products can be achieved by regulating the system pressure. Also, adjusting the through-put (residence time a liquid hourly space velocity ) gives further control of product distribution and degree of olefin conversion.

The temperature in the reactor is determined by the boiling point of the liquid mixture present at any given pressure. The temperature in the lower portions of the colum will reflect the constitution of the material in that part of the column, which will be higher than the overhead; that is, at constant pressure a change in the temperature of the system indicates a change in the composition in the column. To change the temperature the pressure is changed. Temperature control in the reaction zone is thus controlled by the pressure; by increasing the pressure, the temperature in the system is increased, and vice versa. It can also be appreciated that in catalytic distillation as in any distillation there is both a liquid phase (internal reflux) and a vapor phase. Thus, the reactants are partially in liquid phase which allows for a more dense concentration of molecules for reaction, whereas, the concurrent fractionation separates product and unreacted materials, providing the benefits of a liquid phase system (and a vapor phase system) while avoiding the detriment of having all of the components of the reaction system continually in contact with the catalyst which would limit the conversion to the equilibrium of the reaction system components.

DETAILED DESCRIPTION OF THE INVENTION

The olefins may be $C_2$ to $C_{20}$ olefins, preferably $C_2$ $C_{12}$ olefins, including normal and branched forms thereof. For example, suitable olefins are ethylene, propylene, butylene, isobutylene, 1-pentene, 1-hexene, 2-hexene, 2, 3-dimethyl-1-pentene, 1-octene, diisobutylene, 1-nonene and 1-decene, dodecene and the like.

The olefins may oontain substituents which do not interfere with the alkylation. In one preferred embodiment the olefin is a $C_2$ to $C_4$ olefin.

In some reactions according to the present 20 invention, the olefin will be a higher boiling material than the organic aromatic compound, e.g., $C_8$ to $C_{20}$ olefins. In such instances any unreacted olefin will appear in the bottoms alkylation product, although a side draw may be used to reduce such material in the product to product to an insignificant level. However, operating the reaction with far less than a stoichiometric amount of olefin in the reaction zone, as described, will normally keep the olefin. Level in the bottoms low or entirely eliminated.

In those instances wherein the olefin is lower boiling than the organic aromatic compound, e.g., $C_2$ to $C_7$ is compound the large molar excess present in the reaction zone. In those instances the overhead may be condensed to remove a major portion of the organic aromatic compound and the olefin and inerts removed for further separation or use. Similarly inerts such as the alkane of the particular olefin(s) which are often found in olefin streams will be a possible contaminant depending on its boiling point in either the bottoms or overhead. The organic aromatic compounds are preferably those having a boiling point of 250° C. or less under the pressure conditions of the distillation column reactor. The organic aromatio compounds include hydrocarbons of one or more rings and 6 to 20 carbon atoms which may contain substituents which do not interfere with the alkylation including halogen (Cl, Br, F and I), OH and alkyl, cycloalkyl, aralkyl and alkaryl radicals of 1 to 10 carbon atoms. Suitable organic aromatic compounds include benzene, xylene, toluene, phenol, cresol, ethyl benzene, diethyl benzene, naphthalene, indene, phenyl bromide, 1-bromo-2-chloro-benzene, 1-bromo-4-cyclohexyl benzene, 2-bromo-1,4-dihydroxy-benzene, 1(bromo-methyl) naphthalene, 1,2-dihydronaphthalene and the like, a preferred group of compounds for use in the present process is benzene, xylene, toluene, phenol, and cresol.

The mole ratio of organic aromatic compound to olefin may be in the range of 2 to 100:1, preferably 2 to 50:1 and more desirably about 2 to 10:1. The greater the excess of organic aromatic compound the more the selectivity to the monosubstituted product is improved. Alkylation is forced to completion, since the simultaneous and concurrent fractionation and removal of the alkylation product from the distillation column reactor does not allow the products to contribute to the reverse reaction (Le Chatelier's Principle). However, very large molar excesses of organic aromatic compounds require a very high reflux ratio, and a low unit productivity. Hence, the correct ratio of organic aromatic compound to olefin must be determined for each combination of reactants as well as the acceptable olefin content in either the overhead or alkylation product (as described above), in a particular embodiment which is of current commercial importance ethylene or propylene is reacted with benzene according to the present invention to form ethyl benzene or cumene, respectively. In both of these reactions the olefin is the most volatile component and it is desirable to react it rather than have some carried off overhead. The presence of ethylene, propylene or other lower boiling olefin in the tower with benzene will result in a small but detectable temperature depression in the tower where such lower boiling olefins are present as entities and unreacted. As the ethylene, propylene or other lower boiling olefin in reacted with benzene, the depressing effect is diminished and furthermore, the reactions which is exothermic also diminishes the effect. The magnitude of the temperature depression immediately above the olefin feed is a measure of the concentration of ethylene or other lower boiling olefin in the system, that is, the larger the concentration of the lower boiling olefin, the greater the depression of the temperature where the benzene had olefin are initially together and yet unreacted. For any particular system the concentration of tHe olefin to provide a given temperature depression can be determined and plotted. Thus, by maintaining a specific temperature at point of maximum temperature depression by adjusting the olefin feed, a given ratio of olefin to benzene can be maintained in a simple and expedient manner. More significantly, the maintenance of the depression at a given temperature can assure that substantially all of the olefin will be reacted prior to the end of the catalyst bed and overhead exit, if the corresponding, olefin concentration has been determined to produce that effect.

This same control system can be employed in regard to any combination of lower boiling olefin and higher boiling organic aromatic compound.

The length of the catalyst bed, particularly that portion wherein the reactants are in contact and the major portion of the reaction occurs, depends on the reactants, location of the olefin feed and the acceptable unreacted. Olefin in the streams leaving the tower. Some degree of development testing will be required for each set of reactants and parameters of stream purity following present disclosures.

The present alkylation reaction can be carried out at sub-through super atmospheric pressure, e.g., 0.20 to 40 atmospheres. The temperature will vary depending on the reactants and product. Furthermore, the temperature along the column will be as in any distillation column, the highest temperature will be in the bottom and the temperature along the column will be the boiling point of the compositions at that point in the column under the particular conditions of pressure. Moreover, the exothermic heat of reaction does not change the temperature in the column, but merely causes more boil up. However, the temperatures within the column with the above considerations in mind will generally be in the range of 50° C. to 500° C., preferably 70° C. to 500° C. for the mole sieve and 70° C. to 200° C. for the cation exchange resin, and more preferably in the range of about 80° C. to 300° C. at pressures of 0.5 to 20 atmospheres for the mole sieve, and about 80° C. to 150° C. at 0.25 to 15 atmospheres for the resin catalyst.

Molecular sieves are porous crystalline, three-dimensional alumina-silicates of the zeolite mineral group. The crystal skeleton is composed of silicon and aluminum atoms each surrounded by four oxygen atoms to form The term molecular sieve Can be applied to both naturally occurring zeolites and synthetic zeolites. Naturally occurring zeolites have irregular pore size and are not generally considered as equivalent to synthetic zeolites. In the present invention, however, naturally occurring zeolites are acceptable so long as they are substantially pure. The balance of the present discussion shall be directed to the synthetic zeolites with the understanding that natural zeolites are considered equivalent thereto as indicated above, i.e. in so far as the natural zeolites are the functional equivalents to the synthetic zeolites.

Usually synthetic zeolites are prepared in the 15 sodium form, that is, with a sodium cation in close proximity to each aluminum tetrahedron and balancing its charge. To date seven principal types of molecular sieves have been reported, A, X, Y, L, erionite, omega and mordenite. The A type have relative small pore size. By the term pore size is meant the effective pore size (diameter) rather than the free pore size (diameter). Types X and Y have larger pore size (approximately 10 A.) and differ as to the range of ratio of $Al_2O_3$ to $SiO_2$ as:

Type X—$Al_2O_3$/2.0–3.0 $SiO_2$ Type
Y—$Al_2O_3$/3.0–6.0 $SiO_2$

Type L and the other types listed have still higher ratios of $SiO_2$ to $Al_2O_3$.

The mole sieve catalysts employed in the present invention are the acid form mole sieves or exhibit acidic characteristics. The acid form of the mole sieves is commercially available, but also may be prepared by treating the mole sieves with acid to exchange Na for hydrogen. Another method to produce the acid form is to treat the mole sieve with decomposable cations (generally ammonium ions) to replace Na with the decomposable ions and thereafter to heat the mole sieve to decompose the cation leaving the acid form. Generally the Na form mole sieve is treated with ammonium hydroxide to remove the Ma and thereafter the mole sieve is heated to a temperature of about 350° C. to remove of the ammonia. The removal of $Na^+$ ions with $NH^+_4$ is more easily carried out than with multivalent ions as described below and these catalysts are generally more active, but less stable to heat than the multivalent cation exchange forms. Mole sieves, which have had their alkali metal reduced to low levels by partial treatment with $NH^+_4$ and partial multivalent metal cation exchange, possess increased activity and increased stability. In addition to mole sieves which are acidic according to the Bronsted Theory those mole sieves which exhibit acidic characteristics under the Lewis Theory, for example, calcium exchanged mole sieves are suitable for the present reaction. By exchanging the univalent cations (e.g.) $Na^+$) with multivalent cation, strong ionic activity is imarted. The ratio of $SiO_2$: $Al_2O_3$ Valence and radius of the cation and the extent of exchange all affect the catalyst activity. In general activity increases with (1) increased $SiO_2$ $Al_2O_3$ ratio, (2) decreased cation radius and an increase in cation valence. The effect of replacing univalent ions (e.g. $Na^+$) with bivalent (e.g. $Ca^{++}$) is much greater than replacing the bivalent ions with cations of greater valence.

The various types of mole sieves having reduced alkali metal content are characterized as the acid form molecular sieve and are all contemplated as useful in the present invention.

It would appear that the pore size within the crystal lattice may affect the selectivity. According to one theory of molecular sieve catalytic activity, zeolite catalysis occurs primarily inside the uniform crystal cavities, consequently zeolitic catalyst activity depends on the number of aluminum atoms in the crystal and thus on the chemical composition of the crystal. Moreover, these catalytic sites are fixed within the rigid structure of the crystal, so that access to site can be altered by altering the structure of the crystal.

The acid form mole sieves are generally produced and available as particles in the range of <10 micron (powders) to 0.2 inch in diameter (beads).

In this form the mole sieves form too compact a bed and will not function adequately in a distillation, since there is a very large pressure drop through the bed and the free flow of internal reflux and rising vapor is impeded. Mole sieves in the shape of conventional distillation structures, such as rings, saddles, and the like may be used in the present invention. The particulate mole sieves may be employed by enclosing them in a porous container such as cloth, screen wire or polymeric mesh. The material used to make the container must be inert to the reactants and conditions in the reaction system. The cloth may be any material which meets this requirement such as cotton, fiber glass, polyester, nylon and the like. The screen wire may be aluminum, steel, stainless steel and the like. The. Polymer mesh may be nylon, teflon or the like. The mesh or threads per inch of the material used to make the container is such that the catalyst is retained therein and will not pas through the openings in thermal aerial. Particles of about 0.15 mm size or powders may be used and particles up to about ¼ inch diameter may be employed in the containers.

Suitable acid cation exchange resins include those which contain sulfonic acid groups, and which may be obtained by polymerization or copolymerization of aromatic vinyl compounds followed by sulfonation. Examples of aromatic vinyl compounds suitable for preparing polymers or copolymers are: styrene, vinyl toluene, vinyl naphthalene, vinyl ethylbenzene, methyl styrene, vinyl chlorobenzene and vinyl xylene. A large variety of methods may be used for preparing these polymers; for example, polymerization alone or in admixture with other monovinyl compounds, or by crosslinking with polyvinyl compounds; for example, with divinyl benzene, divinyl toluene, divinylphenylether and others. The polymers may be prepared in the presence or absence of solvents or dispersing agents, and various polymerization initiators may be used, e.g., inorganic or organic peroxides, persulfates, etc.

The sulfonic acid group may be introduced into these vinyl aromatic polymers by various known methods; for example, by sulfating the polymers with concentrated sulfuric and chlorosulfonic acid, or by copolymerizing aromatic compounds which contain sulfonic acid groups (see e.g., U.S. Pat. No. 2,366,007). Further sulfonic acid groups may be introduced into the polymer which aready contain sulfonic acid groups; for example, by treatment with fuming sulfuric acid, i.e., sulfuric acid which contains sulfur trioxide. The treatment with fuming sulfuric acid is.

Preferably carried out at 0° to 150° C. and the Sulfuric acid should contain sufficient sulfur trioxide so that it still contains 10 to 50% free sulfur trioxide after the reaction. The resulting products preferably contain an average of 1.3 to 1.8 sulfonic acid groups per aromatic nucleus. Particularly, suitable polymers which contain sulfonic acid groups are copolymers of aromatic monovinyl compounds with aromatic polyvinyl compounds, particularly, divinyl compounds, in which the polyvinyl benzene content is preferably 1 to 20% by weight of the copolymer (see, for example, German Patent Specification No. 908,240). The ion exchange resin is generally used in a granular size of about 0.25 to 1 mm, although particles from 0.15 mm up to about 2 mm may be employed. The finer catalysts provide high surface area, but also result in high pressure drops through the reactor, The macroreticular form of these catalysts have much larger surface area exposed and limited swelling which all of these resins undergo in a non-aqueous hydrocarbon medium compared to the gelular catalysts.

The container employed to hold the catalyst particles may have any configuration, such as the pockets disclosed in the commonly assigned patents above or the container may be a single cylinder, sphere, doughnut, cube, tube or the like.

Each container containing a solid catalytic material comprises a catalyst component. Each catalyst component is intimately associated with a spacing component which is comprised of at least 70 volume % open space up to about 95 volume % open space. This component may be rigid or resilient or a combination thereof. The combination of catalyst component and spacing component form the catalytic distillation structure. The total volume of open space for the catalytic distillation structure should be at least 10 volume % and preferably at least 20 volume % up to about 65 volume %. Thus desirably the spacing component or material should comprise about 30 volume % of the catalytic distillation structure, preferably about 30 volume % to 70 volume %. Resilient materials are preferred. One suitable such material is open mesh knitted stainless wire, known generally as demister wire or an expanded aluminum. Other resilient components may be similar open mesh knitted polymeric filaments of nylon, teflon and the like. Other 5 materials such as highly open structures foamed material, e.g., reticulated polyurethane foam (rigid or resilient) may be formed in place or applied around the catalyst component. In the case of larger catalyst components such as 10 from about ¼ inch to ½ pellets, spheres, pills and the like each such larger component may be individually intimately associated with or surrounded by the spacing component as described above, it is not essential that the spacing component, entirely cover the catalyst component. It is only necessary that the spacing component intimately associated with the catalyst component will act to space the various catalyst components away from one another as described above. Thus, the spacing component provides in effect a matrix of substantially open space in which the catalyst components are randomly but substantially evenly distributed.

A preferred catalytic distillation structure for use herein comprises placing the mole sieve or cation exchange resin particles into a plurality of pockets in a cloth belt, which is supported in the distillation column reactor by open mesh knitted stainless steel wire by twisting the two together in a helical form. This allows the requisite flows and prevents loss of catalysts the cloth may be an material which is inert in the reaction. Cotton or linen are useful: but fiber glass cloth or "Teflon" cloth are preferred.

In the following examples the catalyst packing 5 consisted of bags in the form of a fiber glass cloth belt approximately six inches wide with narrow pockets approximately ¾ inch wide sewn across the belt. The pockets are spaced about ¼ inch apart. These pockets are filled with the catalyst particles to form approximately cylindrical containers, and the open ends are then sewn closed to confine the particles. This belt is then twisted into a helical form to fit inside the column. Twisted in with the belt is also a strip of an open mesh knitted stainless steel wire, which serves to separate the mole sieve filled cloth pockets and provide a passage for vapor flow.

The wire mesh provides the support for the catalyst (belt) and provides some degree of vapor passage through the catalyst particles, which otherwise form a very compact bed which has a high pressure drop. Thus, the down flowing liquid is in intimate contact with the rising vapors in the column.

In commercial-scale operations, it is contemplated, 25 catalyst packing would be made up of alternating layers of mole sieve filled cloth belts similar to the ones described above, and a spacing material which could be of any convenient, suitable substance, such as a corrugated wire screen or wire cloth or a knitted wire mesh. The layers would be arranged vertically or horizontally. For simplicity of fabrication and for better distribution of vapor flow passages, a vertical orientation is preferred. The height of a section of this packing should be of any convenient dimension, from a few inches to several feet. For ease of assembly and installation, the packing would be made into sections of the desired shape and size, each section fastened together with circumferential bands of tie wires depending on its size and shape. A complete assembly in a column would consist of several sections, arranged in layers, with possibly the orientation of the catalyst-filled belts turned at right angles in successive layers to improve liquid and vapor flow distribution.

Figure 1:
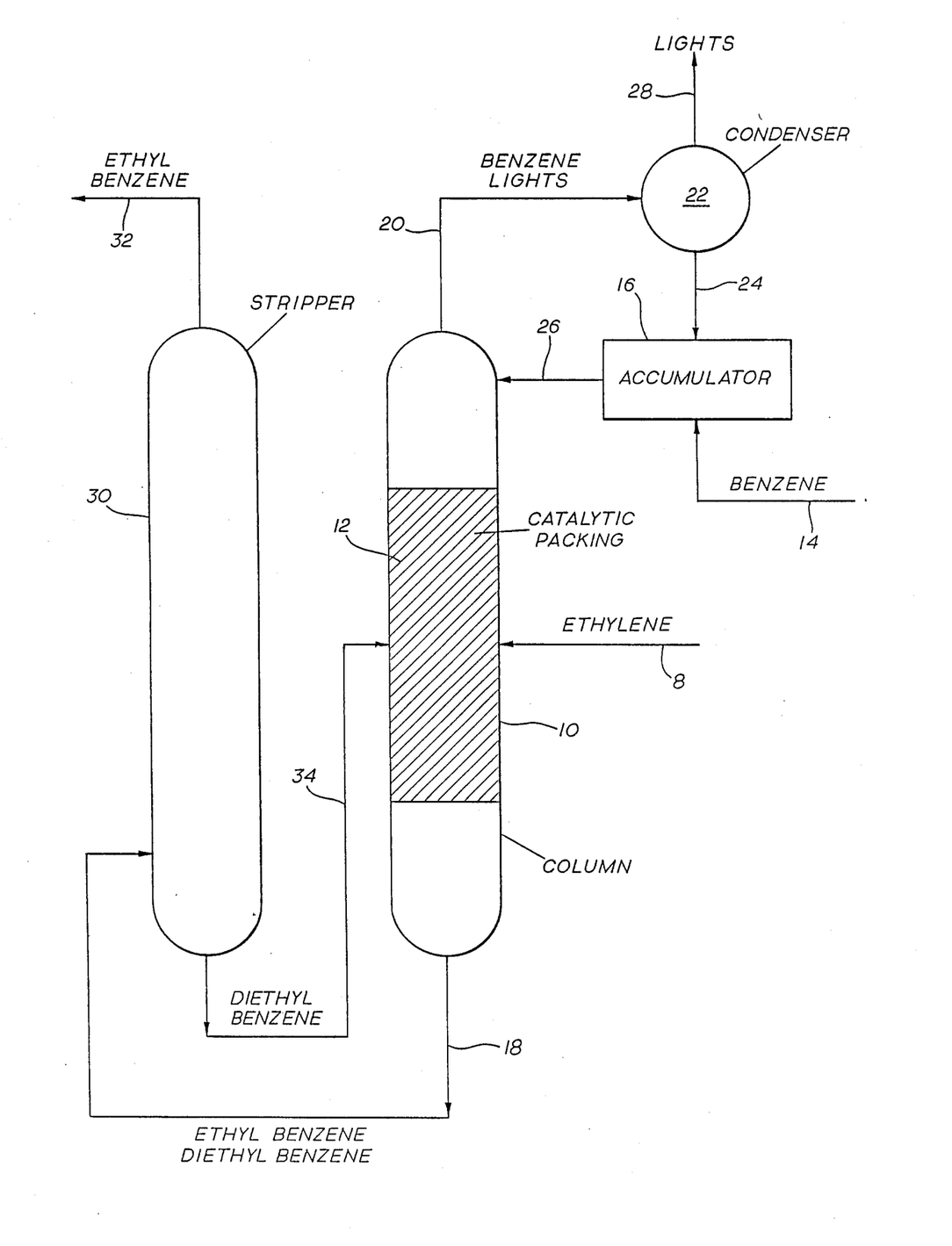
The drawing is a schematic representation of a preferred embodiment of one species of the present invention for producing ethyl benzene.

The drawing illustrates one species of the present invention, i.e., the production of ethylbenzene by alkylating benzene with ethylene and a preferred embodiment of that species. Referring to the drawing distillation column reactor is divided into three sections. In the middle section the catalyst packing (catalytic distillation structures) 12 are positioned as described, Linde molecular sieve LZ-Y82 1/16" (Union Carbide Corp.) is deposited in the pockets of fiber glass belts and formed in to a helix with stainless steel mesh as described.

The reactor 10 is a four inch diameter pilot column 70 feet tall with 35 feet of the catalyst packing in the middle portion. The lower portion of the column is a conventional distillation column Configuration (equivalent 25 trays). Benzene is conveniently added as makeup via 14 into reflux accumulator the benzene can also be added through a separate line (not shown). The ethylene is fed to the column via 8 at about the mid point of the catalyst packing 12 or below the catalyst bed (not show) for better mixing. The ethylene may also be fed at several points to reduce the concentration at any one location in the catalyst zone, thus reducing oligomerization as a side reaction. The reaction is exothermic and initiated by contacting the two reactants in the catalyst packing. Ethyl benzene and diethyl benzene are the principal reaction products. Both of these products are higher boiling than benzene and ethylene and are recovered via 18 as a bottoms product. The feed of ethylene is adjusted such that there is a molar excess of benzene in the reactor, such that the overhead 20 is primarily benzene, the ethylene having been almost totally reacted. In addition to benzene and some ethylene other lights go off overhead. The overhead is passed to condenser 22 which is operated to condense substantially all of the benzene which passes via 24 to accumulator 16 and hence, by reflux via 26 to column 10. The benzene used in the reaction and lost with the lights (which exit condenser 22 via 28) is made up by fresh benzene feed 14.

The bottoms contain a mixture of ethyl benzene and diethyl benzene which pass via 18 to splitter 30, which is a conventional distillation column operated to fractionate ethyl benzene and diethyl benzene. The ethyl benzene is recovered as overhead 32 and the diethyl benzene recovered as a bottoms product. In this preferred embodiment the diethyl benzene is returned via 34 to the lower portion of the catalyst packing 12 in column 10, although it could be recovered as such.

However, in this preferred embodiment it is desired to maximize ethyl benzene production. There is an equilibrium between benzene and diethyl benzene in the catalyst as:

Benzene + Diethyl Benzene ⇌ Ethyl Benzene

In the lower portion of the catalyst packing there is a large volume of benzene along with the reaction products and the recycled diethyl benzene, hence, the reversible reaction favors the production of ethyl benzene, which is being continuously removed from the catalytic zone.

Such conventional items as valves, reboilers, slip streams, etc. are not shown, but would be obvious expedients to those setting up such equipment.

EXAMPLE 1

The reactor was a 1 inch, six foot stainless tube, composed of 2 foot sections bolted together. The bottom and top two feet contained conventional distillation packing, the middle two feet contained mole sieve in pockets (four pockets twisted with demister wire as described above: Benzene was fed under nitrogen pressure through a rotameter to the tower about 6" above the top of the catalyst bed. The olefin, either ethylene or propylene was fed to the bottom (below) of the catalyst bed losing a micrometering valve. The rate of feed of olefin was adjusted to maintain the tower pressure with slow constant bleed of gas overhead. The rate of olefin addition was slightly larger than the rate of reaction. The benzene feed rate and bottoms withdraw rate are related. The benzene rotameter was set at a given value and the bottom withdrawal rate was adjusted to maintain a constant bottoms level.

The catalyst was dried initially by taking off some benzene and water overhead and an occasional small amount of liquid material was taken off overhead during runs to maintain the dry catalyst and to remove any low boiling by-products. Bottoms samples were analyzed by, gas liquid phase chromatography using 50 meter SE-30 capillary column 20 and FID.

The conditions and results of several runs are set forth in TABLE I.

EXAMPLE 2

Using the same reactor as described in EXAMPLE 1, but with Amberlyst 15 (acidic cation exchange resin) as the catalyst in the cloth pockets of the catalytic distillation structure several runs were carried out to produce cumene using propylene and ethyl benzene. The conditions and results are set out in TABLE II.

TABLE I

| | RUN NO. | | | | | | | | | |
|---|---|---|---|---|---|---|---|---|---|---|
| | 1 | 2 | 3 | 4 | 5 | 6 | 7 | 8 | 9 | 10 |
| Catalyst | Y-82* | Y-82* | Y-82* | SK-500* | SK-500* | Y-82* | Y-82* | Y-82* | SK-500* | SK-500* |
| Olefin Feed | C3 | C3 | C3 | C3(c) | C3(c) | C2 | C2 | C2 | C2 | C2 |
| Pressure, PSIG | 70 | 75 | 123 | 120 | 120 | 130 | 170 | 220 | 220 | 250 |
| TEMP. F.: | | | | | | | | | | |
| Bottoms | 355 | 470 | 540 | 410 | 455 | 475 | 550 | 560 | 440 | 480 |
| Lower Cat. Bed | 300 | 300 | 341 | 308 | 320 | 343 | 358 | 380 | 340 | 390 |
| Upper Cat. Bed | 286 | 280 | 330 | 296 | 282 | 325 | 320 | 350 | 294 | 328 |
| Recovery Rate | | | | | | | | | | |
| Overhead | (a) | (a) | (a) | (a) | (a) | (a) | (a) | (a) | (a) | (a) |
| Bottoms, G./Hr. | 131 | 165 | 300 | 283 | Sample No Take Off | 200 | 38.4 | 225 | 56 | 93 |
| Bottoms Analysis: Wt. % | | | | | | | | | | |

TABLE I-continued

| | RUN NO. | | | | | | | | | |
|---|---|---|---|---|---|---|---|---|---|---|
| | 1 | 2 | 3 | 4 | 5 | 6 | 7 | 8 | 9 | 10 |
| Benzene | 73.3 | 30.2 | 72.5 | 62.6 | 45.2 | 92.9 | 65.9 | 86.1 | 93.9 | 80.7 |
| Ethylbenzene | — | — | — | — | — | 6.7 | 31.8 | 12.5 | 5.4 | 16.4 |
| Cumene | 23.01 | 50.4 | 25.1 | 34.8 | 50.4 | — | — | — | — | — |
| Diethylbenzene | — | — | — | — | — | 0.1 | 1.7 | 0.7 | 0.3 | 1.2 |
| Dipropyl Benzene | 1.7 | 13.2 | 1.0 | 1.1 | 3.4 | — | — | — | — | — |
| Polyethylbenzene | — | — | — | — | — | 0.2 | 0.5 | 0.6 | 0.3 | 0.6 |
| Polypropyl Benzene | 2.4 | 3.7 | 1.1 | Trace | Trace | — | — | — | — | — |
| Other (d) | Trace | 2.5 | 0.1 | 1.4 | 0.9 | 0.0 | 0.1 | 0.1 | 0.1 | 0.9 |
| Production Rate G. | | | | | | | | | | |
| Ethylbenzene/G.Cat.Hr | — | — | — | — | — | 0.13 | 0.12 | 0.28 | 0.04 | 0.22 |
| Cumene/G. Cat. Hr. | 0.30(b) | 0.83 | 0.75 | 1.4 | — | — | — | — | — | — |
| Length of Run, Min. | 39 | 65 | 52 | 18 | — | 12 | 50 | 20 | 75 | 55 |

*Sold By Union Carbide Corp. (Acidic Molecular Sieve)
(a) Olefin Fed At A Rate To Maintain Pressure With A Slow bleed Overhead.
(b) Catalyst Not Dried Sufficiently.
(c) Contained Propylene: Propane = 58/42 Wt. %
(d) Oligomers and other unidentified products

TABLE II

| | RUN | | |
|---|---|---|---|
| | 11 | 12 | 13 |
| Catalyst | Amberlyst 15 | Amberlyst 15 | Amberlyst 15 |
| Olefin Feed | $C_3$ | $C_3$ | $C_3$ |
| Pressure, psig | 40 | 20 | 25 |
| Temp °F. | | | |
| Bottoms | 405 | 335 | 387 |
| Lower Cat. bed | 255 | 215 | 228 |
| Upper Cat. bed | 215 | 215 | 225 |
| Recovery Rate, g/hr | | | |
| Overhead | (a) | (a) | (a) |
| Bottoms | 75 | 156 | 106 |
| Bottoms Analysis, Wt. % | | | |
| Benzene | 27.1 | 47.1 | 50.2 |
| Cumene | 64.2 | 46.0 | 45.8 |
| Dipropyl Benzene | 5.0 | 2.1 | 0.1 |
| Unknown | 2.8 | 3.5 | 3.1 |
| Production Rate g. Cumene/g. cat./hr. | 0.7 | 1.0 | 1.3 |
| Length of Run, Min. | 60 | 34 | 52 |

(a) Olefin fed at a rate to maintain pressure with a slow bleed overhead

The invention claimed is:

1. A method for controlling the concentration of olefin in the alkylation of organic aromatic compounds comprising:
(a) concurrently
  (i) feeding a $C_2$ to $C_{20}$ olefin into a fixed bed acidic catalytic distillation structure in a distillation reaction zone located in a distillation column reactor and having process flow rates
  (ii) contacting said olefin with an organic aromatic compound having a boiling point higher than said olefin thereby catalytically reacting said organic aromatic compound and said olefin to form an alkylation product there being a temperature depression in said distillation column reactor at a point immediately above the point at which said olefin is fed thereto,
  (iii) determining the concentration of said olefin in said reactor at a given temperature depression at a given pressure,
  (iv) adjusting the process flows rate in the distillation column reactor to maintain a selected temperature at said depression point whereby a specific mole ratio of organic aromatic compound to olefin is maintained and
  (v) fractionating the resultant alkylation product and the unreacted organic aromatic compound and olefin in said fixed bed, and
(b) withdrawing said alkylation product from said distillation column reactor at a point below said fixed bed.

2. The process according to claim 1 wherein a molar excess of organic aromatic compound to olefin is present.

3. The process according to claim 2 wherein from 2 to 100 moles of organic aromatic compound per mole of olefin are present.

4. The process according to claim 3 wherein from 2 to 50 moles of organic aromatic compound per mole of olefin are present.

5. The process according to claim 4 wherein from 2 to 10 moles of organic aromatic compound per mole of olefin are Present.

6. The process according to claim 2 wherein unreacted organic aromatic compound is recovered as an overhead and a portion thereof returned to said distillation column reactor.

7. The process according to claim 1 wherein said organic aromatic compound has 6 to 20 carbon atoms.

8. The process according to claim 1 wherein said organic aromatic compound has a boiling point of 250° C. or less under the pressure conditions in said distillation column reactor.

9. The process according to claim 1 wherein said pressure in said distillation column reactor is in the range of 0.25 to 40 atmospheres.

10. The process according to claim 9 wherein the temperature is in the range of 50° C. to 500° C.

11. The process according to claim 9 wherein said pressure is in the range of 0.5 to 20 atmospheres.

12. The process according to claim 11 wherein the temperature is in the range of 50° C. to 300° C.

13. The process according to claim 7 wherein said olefin is a $C_2$ to $C_7$ olefin.

14. The process according to claim 7 wherein said olefin is a $C_8$ to $C_{20}$ olefin.

15. The process according to claim 7 wherein said organic aromatic compound is benzene, xylene, toluene, phenol or cresol.

16. The process according to claim 15 wherein said organic aromatic compound is benzene.

17. The process according to claim 15 wherein said organic aromatic compound is phenol.

18. The process according to claim 15 wherein said olefin is a $C_2$ to $C_4$ olefin.

19. The process according to claim 16 wherein said olefin is ethylene.

20. The process according to claim 16 wherein said olefin is propylene.

21. The process according to claim 1 wherein process flow rates comprise olefin feed, organic aromatic compound feed, organic aromatic compound overhead, organic aromatic compound reflux, olefin overhead, alkylation product withdrawal.

22. The process according to claim 1 wherein said olefin feed rate is adjusted.

23. The process according to claim 16 wherein said olefin is isopropylene.

* * * * *

UNITED STATES PATENT AND TRADEMARK OFFICE
CERTIFICATE OF CORRECTION

PATENT NO. : 4,849,569

DATED : July 18, 1989

INVENTOR(S) : Lawrence A. Smith, Jr.

It is certified that error appears in the above—identified patent and that said Letters Patent is hereby corrected as shown below:

Column 1, Line 12 reads "Serial Number 689,444" but should read --- Serial Number 689,445 ---

Column 1, Line 29 reads "4,232,530:" but should read --- 4,232,177 ---

Column 1, Line 29-30 reads "4:242,530; 4,250,052; 4,302/356 and 4;307;254" but should read --- 4,242,530, 4,250,052; 4,302,256; and 4,307,254 ---

Column 1, Line 50 reads "20" but should be omitted

Column 1, Line 52 reads "4" but should be omitted

Column 1, Line 62 reads "Catalytic" but should read --- catalytic ---

Column 2, Lines 58 and 59, delete "success of catalytic distilation lies in an understanding"

Column 3, Line 9 reads "a" but should read --- = ---

Column 3, Line 52 reads "20" but should be omitted

Column 3, Line 57 reads "product to" second occurence but should be omitted

Column 3, Line 64-65 reads "is compound the" but should read --- there may be some olefin going overhead even with the ---

Column 4, Line 51 reads "reactions" but should read --- reaction ---

UNITED STATES PATENT AND TRADEMARK OFFICE
CERTIFICATE OF CORRECTION

PATENT NO. : 4,849,569

DATED : July 18, 1989

INVENTOR(S) : Lawrence A. Smith, Jr.

It is certified that error appears in the above—identified patent and that said Letters Patent is hereby corrected as shown below:

Column 4, Line 60 reads "tHe" before "olefine" but should read --- the ---

Column 5, Line 37 reads after "form" but should read --- form a small pyramid or tetrahedron (tetrahedral coordination). ---

Column 5, Line 37 reads "Can" but should read --- can ---

Column 5, Line 48 reads "15" but should be omitted

Column 6, Line 7 reads "Ma" but should read --- Na ---

Column 6, Line 24 reads "Valence" but should read --- valence ---

Column 6, Line 64 reads "The. Polymer" but should read --- The polymer ---

Column 6, Line 68 reads "thermal aerial" but should read --- the material ---

Column 7, Line 30 reads "delete the period" but should read --- preferably carried out at 0 to 150°C and the sulfuric ---

Column 7, Line 31 reads "Preferably carried out at 0 to 150°C. and the Sulfuric" but should read Column 8, Line 7 reads "5" but should be omitted Column 8, Line 11 reads "10" but should be omitted Column 8, Line 30-31 reads "catalyst the cloth may be an" but should read --- catalysts. The cloth may be any ---

UNITED STATES PATENT AND TRADEMARK OFFICE
CERTIFICATE OF CORRECTION

PATENT NO. : 4,849,569

DATED : July 18, 1989

INVENTOR(S) : Lawrence A. Smith, Jr.

It is certified that error appears in the above—identified patent and that said Letters Patent is hereby corrected as shown below:

Column 8, Line 32 reads ":" but should read --- , ---

Column 8, Line 34 reads "5" but should be omitted

Column 8, Line 53 reads "25" but should be omitted

Column 9, Line 9 reads "reactor" but should read --- 10 ---

Column 9, Line 11 reads "are" but should read --- is ---

Column 9, Line 19 reads "Configuration" but should read --- configuration ---

Column 9, Line 21 reads "accumulator" but should read --accumulator 16.--

Column 9, Line 21 reads "the" but should read --- The ---

Column 10, Line 38 reads "15" but should be omitted

UNITED STATES PATENT AND TRADEMARK OFFICE
CERTIFICATE OF CORRECTION

PATENT NO. : 4,849,569

DATED : July 18, 1989

INVENTOR(S) : Lawrence A. Smith, Jr.

It is certified that error appears in the above-identified patent and that said Letters Patent is hereby corrected as shown below:

Column 10, Line 43 after "by" delete ","

Signed and Sealed this

Second Day of April, 1991

*Attest:*

HARRY F. MANBECK, JR.

*Attesting Officer*  Commissioner of Patents and Trademarks